(12) United States Patent
Rafalski et al.

(10) Patent No.: US 6,642,435 B1
(45) Date of Patent: Nov. 4, 2003

(54) PLANT FOLATE BIOSYNTHETIC GENES

(75) Inventors: J. Antoni Rafalski, Wilmington, DE (US); Zude Weng, Wilmington, DE (US); Leslie T. Harvell, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/465,559

(22) Filed: Dec. 17, 1999

Related U.S. Application Data

(60) Provisional application No. 60/112,735, filed on Dec. 18, 1998.

(51) Int. Cl.$^7$ .................. A01H 3/00; C07H 21/04; C12N 5/14; C12N 9/00
(52) U.S. Cl. .............. 800/278; 435/69.2; 435/183; 435/410; 435/419; 435/252.3; 435/320.1; 530/350; 530/370; 536/23.1; 536/23.2; 536/23.6; 536/24.1; 536/24.33; 800/295; 800/281
(58) Field of Search ................. 435/69.2, 183, 435/410, 419, 252.3, 320.1; 530/350, 370; 536/23.1, 23.2, 23.6, 24.1, 24.33; 800/278, 295, 281

(56) References Cited

U.S. PATENT DOCUMENTS 5,597,717 A * 1/1997 Guerineau et al.

FOREIGN PATENT DOCUMENTS

WO  WO9808542  * 3/1998

OTHER PUBLICATIONS

Bork, P. Genome Research, 200, vol. 10, p. 398–400.*
NCBI General Identifier No. 141435.
J. Bacteriol., 172(12):7211–7226 (1990) Slock et al.
DNA Res. 1(1):1–14, (1994) Ogasawara et al.
NCBI General Identifier No. 1934972.
EMBO J., 16(5):947–957 (1997) Rebeille et al.
NCBI General Identifier No. 4938476.
NCBI General Identifier No. 6143861.
NCBI General Identifier No. 4826728.
PNAS 89:9151–9155 (1992) Garrow et al.
NCBI General Identifier No. 1709377.
Hennig et al. (1998) Nat. Structu. Biol. 5(5):357–362.
Shane et al. (1987) Biochemistry 26(2):504–512.

* cited by examiner

*Primary Examiner*—Phuong T. Bui

(57) ABSTRACT

This invention relates to an isolated nucleic acid fragment encoding a folate biosynthetic enzyme. The invention also relates to the construction of a chimeric gene encoding all or a portion of the folate biosynthetic enzyme, in sense or antisense orientation, wherein expression of the chimeric gene results in production of altered levels of the folate biosynthetic enzyme in a transformed host cell.

12 Claims, No Drawings

US 6,642,435 B1

PLANT FOLATE BIOSYNTHETIC GENES

This application claims the benefit of U.S. Provisional Application No. 60/112,735, filed Dec. 18, 1998.

FIELD OF THE INVENTION

This invention is in the field of plant molecular biology. More specifically, this invention pertains to nucleic acid fragments encoding folate biosynthetic enzymes in plants and seeds.

BACKGROUND OF THE INVENTION

Tetrahydrofolic acid and its derivatives $N^5,N^{10}$-methylenetetrahydrofolate, $N^5,N^{10}$-methenyltetrahydrofolate, $N^{10}$-formyltetrahydrofolate and $N^5$-methyltetrahydrofolate are biologically active forms of folic acid. The tetrahydrofolates are coenzymes that function in a variety of enzyme catalyzed reactions as specialized cosubstrates for one-carbon metabolism. For example, tetrahydrofolate plays an important role in nucleic acid biosynthesis by serving as the immediate source of one-carbon units in purine and pyrimidine biosynthesis. The cellular tetrahydrofolate coenzyme pool must be maintained at specific levels to assure one-carbon metabolism operates efficiently. Thus, one of the most important reactions of the cell is the reduction of dihydrofolate to tetrahydrofolate by dihydrofolate reductase. The importance of this reaction in mammalian cells can be shown by the fact that methorexate, a very effective chemotherapy drug, is a potent inhibitor of dihydrofolate reductase (Zubay, G. (1983) *Biochemistry*, Addison-Wesley Publishing Co. Reading, Mass.). Other enzymes involved in the folic acid biosynthetic pathway to maintain the tetrahydrofolate coenzyme pool are tetrahydrofolypolyglutamate synthase, dihydropteroate synthase and dihydroneopterin aldolase.

There is a great deal of interest in identifying the genes that encode proteins required for tetrahydrofolate biosynthesis in plants. These genes may be used in plant cells to alter the tetrahydrofolate coenzyme pool concentration and modulate one-carbon metabolism. Accordingly, the availability of nucleic acid sequences encoding all or a portion of the tetrahydrofolypolyglutamate synthase, dihydropteroate synthase and dihydroneopterin aldolase enzymes would facilitate studies to better understand one-carbon metabolism in plants, provide genetic tools to one-carbon metabolism. The tetrahydrofolate biosynthetic enzymes may also provide targets to facilitate design and/or identification of inhibitors of cell cycle that may be useful as herbicides.

SUMMARY OF THE INVENTION

The present invention relates to isolated polynucleotides comprising a nucleotide sequence encoding a polypeptide of at least 131 amino acids that has at least 80% identity based on the Clustal method of alignment when compared to a polypeptide selected from the group consisting of a corn dihydroneopterin aldolase polypeptide of SEQ ID NO:2, a soybean dihydroneopterin aldolase polypeptide of SEQ ID NO:4 and a wheat dihydroneopterin aldolase polypeptide of SEQ ID NO:6. The present invention also relates to an isolated polynucleotide comprising the complement of the nucleotide sequences described above.

The present invention relates to isolated polynucleotides comprising a nucleotide sequence encoding a polypeptide of at least 75 amino acids that has at least 80% identity based on the Clustal method of alignment when compared to a polypeptide selected from the group consisting of a corn dihydropteroate synthase/dihydropteroate pyrophosphorylase polypeptide of SEQ ID NO:8, a rice dihydropteroate synthase/dihydropteroate pyrophosphorylase polypeptide of SEQ ID NO:10 and a soybean dihydropteroate synthase/dihydropteroate pyrophosphorylase polypeptide of SEQ ID NO:12. The present invention also relates to an isolated polynucleotide comprising the complement of the nucleotide sequences described above.

The present invention relates to isolated polynucleotides comprising a nucleotide sequence encoding a polypeptide of at least 553 amino acids that has at least 80% identity based on the Clustal method of alignment when compared to a corn tetrahydrofolylpolyglutamate synthase/folylpolyglutamate synthase polypeptide of SEQ ID NO:14. The present invention also relates to an isolated polynucleotide comprising the complement of the nucleotide sequences described above.

The present invention relates to isolated polynucleotides comprising a nucleotide sequence encoding a polypeptide of at least 133 amino acids that has at least 80% identity based on the Clustal method of alignment when compared to a polypeptide selected from the group consisting of a corn tetrahydrofolylpolyglutamate synthase/folylpolyglutamate synthase polypeptide of SEQ ID NO:16 and a soybean tetrahydrofolylpolyglutamate synthase/folylpolyglutamate synthase polypeptide of SEQ ID NO:18. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, 13, 15, 17, 19, 21, 23, 25, 27, 29 and 31 that codes for the polypeptide selected from the group consisting of SEQ ID NOs:2, 4, 6, 8, 10, 12, 14, 16, 18, 20, 22, 24, 26, 28, 30 and 32. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a dihydroneopterin aldolase polypeptide of at least 131 amino acids comprising at least 80% homology based on the Clustal method of alignment compared to a polypeptide selected from the group consisting of SEQ ID NOs:2, 4 and 6.

The present invention relates to a dihydropteroate synthase/dihydropteroate pyrophosphorylase polypeptide of at least 75 amino acids comprising at least 80% homology based on the Clustal method of alignment compared to a polypeptide selected from the group consisting of SEQ ID NOs:8, 10 and 12.

The present invention relates to a tetrahydrofolypolyglutamate synthase/folylpolyglutamate synthase polypeptide of at least 553 amino acids comprising at least 80% homology based on the Clustal method of alignment compared to a polypeptide of SEQ ID NO:14.

The present invention relates to a tetrahydrofolypolyglutamate synthase/folylpolyglutamate synthase polypeptide of at least 133 amino acids comprising at least 80% homology based on the Clustal method of alignment compared to a polypeptide selected from the group consisting of SEQ ID NOs: 16 and 18.

The present invention relates to a method of selecting an isolated polynucleotide that affects the level of expression of a dihydroneopterin aldolase, dihydropteroate synthase/dihydropteroate pyrophosphorylase or tetrahydrofolypolyglutamate synthase/folylpolyglutamate synthase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a dihydroneopterin aldolase, dihydropteroate synthase/dihydropteroate pyrophosphorylase or tetrahydrofolypolyglutamate synthase/folylpolyglutamate synthase polypeptide in the host cell containing the isolated polynucleotide; and (d) comparing the level of a dihydroneopterin aldolase, dihydropteroate synthase/dihydropteroate pyrophosphorylase or tetrahydrofolypolyglutamate synthase/folylpolyglutamate synthase polypeptide in the host cell containing the isolated polynucleotide with the level of a dihydroneopterin aldolase, dihydropteroate synthase/dihydropteroate pyrophosphorylase or tetrahydrofolypolyglutamate synthase/folylpolyglutamate synthase polypeptide in the host cell that does not contain the isolated polynucleotide.

The present invention relates to a method of obtaining a nucleic acid fragment encoding a substantial portion of a dihydroneopterin aldolase, dihydropteroate synthase/dihydropteroate pyrophosphorylase or tetrahydrofolypolyglutamate synthase/folylpolyglutamate synthase polypeptide gene, preferably a plant dihydroneopterin aldolase, dihydropteroate synthase/dihydropteroate pyrophosphorylase or tetrahydrofolypolyglutamate synthase/folylpolyglutarnate synthase polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31 and the complement of such nucleotide sequences; and amplifying a nucleic acid fragment (preferably a cDNA inserted in a cloning vector) using the oligonucleotide primer. The amplified nucleic acid fragment preferably will encode a portion of a dihydroneopterin aldolase, dihydropteroate synthase/dihydropteroate pyrophosphorylase or tetrahydrofolypolyglutamate synthase/folylpolyglutamate synthase amino acid sequence.

The present invention also relates to a method of obtaining a nucleic acid fragment encoding all or a substantial portion of the amino acid sequence encoding a dihydroneopterin aldolase, dihydropteroate synthase/dihydropteroate pyrophosphorylase or tetrahydrofolypolyglutamate synthase/folylpolyglutamate synthase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a dihydroneopterin aldolase, dihydropteroate synthase/dihydropteroate pyrophosphorylase or tetrahydrofolypolyglutamate synthase/folylpolyglutamate synthase, the method comprising the steps of: (a) transforming a host cell with a chimeric gene comprising a nucleic acid fragment encoding a dihydroneopterin aldolase, dihydropteroate synthase/dihydropteroate pyrophosphorylase or tetrahydrofolypolyglutamate synthase/folylpolyglutamate synthase, operably linked to suitable regulatory sequences; (b) growing the transformed host cell under conditions that are suitable for expression of the chimeric gene wherein expression of the chimeric gene results in production of dihydroneopterin aldolase, dihydropteroate synthase/dihydropteroate pyrophosphorylase or tetrahydrofolypolyglutamate synthase/folylpolyglutamate synthase in the transformed host cell; (c) optionally purifying the dihydroneopterin aldolase, dihydropteroate synthase/dihydropteroate pyrophosphorylase or tetrahydrofolypolyglutamate synthase/folylpolyglutamate synthase expressed by the transformed host cell; (d) treating the dihydroneopterin aldolase, dihydropteroate synthase/dihydropteroate pyrophosphorylase or tetrahydrofolypolyglutamate synthase/folylpolyglutamate synthase with a compound to be tested; and (e) comparing the activity of the dihydroneopterin aldolase, dihydropteroate synthase/dihydropteroate pyrophosphorylase or tetrahydrofolypolyglutamate synthase/folylpolyglutamate synthase that has been treated with a test compound to the activity of an untreated dihydroneopterin aldolase, dihydropteroate synthase/dihydropteroate pyrophosphorylase or tetrahydrofolypolyglutamate synthase/folylpolyglutamate synthase, thereby selecting compounds with potential for inhibitory activity.

The present invention relates to a composition, such as a hybridization mixture, comprising an isolated polynucleotide or polypeptide of the present invention.

The present invention relates to an isolated polynucleotide of the present invention comprising at least one of 30 contiguous nucleotides derived from a nucleic acid sequence selected from the group consisting of SEQ ID NOs: 1, 3, 5, 7, 9, 11, 13, 15, 17, 19, 21, 23, 25, 27, 29 and 31.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the dihydroneopterin aldolase, dihydropteroate synthase/dihydropteroate pyrophosphorylase or tetrahydrofolypolyglutamate synthase/folylpolyglutamate synthase polynucleotide in an amount sufficient to complement a null mutant and folic acid biosynthesis auxotroph to provide a positive selection means.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:1, 3, 5, 7, 9, 13 and 17 and amino acid sequences SEQ ID NOs:2, 4, 6, 8, 10, 14, 16 and 18 were determined by further sequence analysis of cDNA clones encoding the amino acid sequences set forth in SEQ ID NOs:20, 22, 24, 26, 28, 30 and 32. Nucleotide SEQ ID NOs:19, 21, 23, 25, 27, 29 and 31 and amino acid SEQ ID NOs:20, 22, 24, 26, 28, 30 and 32 were presented in a U.S. Provisional Application No. 60/112,735, filed Dec. 18, 1998.

The sequence descriptions and Sequence Listing attached hereto comply with the rules governing nucleotide and/or amino acid sequence disclosures in patent applications as set forth in 37 C.F.R. §1.821–1.825.

TABLE 1

Folate Biosynthetic Enzymes

| Protein | Clone Designation | SEQ ID NO: (Nucleotide) | SEQ ID NO: (Amino Acid) |
|---|---|---|---|
| Dihydroneopterin aldolase | ccoln.pk075.j3 (FIS) | 1 | 2 |
| Dihydroneopterin aldolase | sdp3c.pk002.o16 (FIS) | 3 | 4 |
| Dihydroneopterin aldolase | wdk1c.pk013.k22 (FIS) | 5 | 6 |
| Dihydropteroate synthase/Dihydropteroate pyrophosphorylase | cr1n.pk0057.a10 (FIS) | 7 | 8 |
| Dihydropteroate synthase/Dihydropteroate pyrophosphorylase | r10n.pk0041.c3 (FIS) | 9 | 10 |
| Dihydropteroate synthase/Dihydropteroate pyrophosphorylase | sdp4c.pk034.b11 (EST) | 11 | 12 |
| Tetrahydrofolylpolyglutamate synthase/Folylpolyglutamate synthase | ccoln.pk061.116 (FIS) | 13 | 14 |
| Tetrahydrofolylpolyglutamate synthase/Folylpolyglutamate synthase | p0006.cbysj94r (EST) | 15 | 16 |
| Tetrahydrofolylpolyglutamate synthase/Folylpolyglutamate synthase | s12.pk123.k13 (EST) | 17 | 18 |
| Dihydroneopterin aldolase | ccoln.pk075.j3 (EST) | 19 | 20 |
| Dihydroneopterin aldolase | sdp3c.pk002.o16 (EST) | 21 | 22 |
| Dihydroneopterin aldolase | wdk1c.pk013.k22 (FIS) | 23 | 24 |
| Dihydropteroate synthase/Dihydropteroate pyrophosphorylase | cr1n.pk0057.a10 (Contig) | 25 | 26 |
| Dihydropteroate synthase/Dihydropteroate pyrophosphorylase | r10n.pk0041.c3 (EST) | 27 | 28 |
| Dihydropteroate synthase/Dihydropteroate pyrophosphorylase | sdp4c.pk034.b11 (EST) | 29 | 30 |
| Tetrahydrofolylpolyglutamate synthase/Folylpolyglutamate synthase | s12.pk123.k13 (EST) | 31 | 32 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs: 1, 3, 5, 7, 9, 11, 13, 15, 17, 19, 21, 23, 25, 27, 29, 31 or the complement of such sequences.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 and the complement of such nucleotide sequences may be used in methods of selecting an isolated polynucleotide that affects the expression of a polypeptide (dihydroneopterin aldolase, dihydropteroate synthase/dihydropteroate pyrophosphorylase or tetrahydrofolypolyglutamate synthase/folylpolyglutamate synthase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed, sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several folate biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other dihydroneopterin aldolase, dihydropteroate synthase/dihydropteroate pyrophosphorylase or tetrahydrofolypolyglutamate synthase/folylpolyglutamate synthase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5'

RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as dihydroneopterin aldolase, dihydropteroate synthase/dihydropteroate pyrophosphorylase or tetrahydrofolypolyglutamate synthase/folylpolyglutamate synthase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (dihydroneopterin aldolase, dihydropteroate synthase/dihydropteroate pyrophosphorylase or tetrahydrofolypolyglutamate synthase/folylpolyglutamate synthase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of folic acid in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics*218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded folate biosynthetic enzyme. An example of a vector for high level expression of the instant polypeptides in a bacterial host is provided (Example 8).

Additionally, the instant polypeptides can be used as a targets to facilitate design and/or identification of inhibitors of those enzymes that may be useful as herbicides. This is desirable because the polypeptides described herein catalyze various steps in folic acid biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1: 174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1 990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
| --- | --- | --- |
| ccoln | Corn Cob of 67 Day Old Plants Grown in Green House* | ccoln.pk075.j3 ccoln.pk061.116 |
| crln | Corn Root From 7 Day Old Seedlings* | crln.pk0057.a10 |
| p0006 | Corn Young Shoot | p0006.cbysj94r |
| r10n | Rice 15 Day Old Leaf* | r10n.pk0041.c3 |
| sdp4c | Soybean Developing Pods (10–12 mm) | sdp4c.pk034.b11 |
| sdp3c | Soybean Developing Pods (8–9 mm) | sdp3c.pk002.o16 |
| s12 | Soybean Two-Week-Old Developing Seedlings Treated With 2.5 ppm chlorimuron | s12.pk123.k13 |
| wdk1c | Wheat Developing Kernel, 3 Days After Anthesis | wdk1c.pk013.k22 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Example 2

Identification of cDNA Clones cDNA clones encoding folate biosynthetic enzymes were identified by conducting BLAST (Basic Local Alignment Search Tool; Altschul et al. (1993) J. MoL Biol. 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Dihydroneopterin Aldolase

The BLASTX search using the EST sequences from clones listed in Table 3 revealed similarity of the polypeptides encoded by the cDNAs to dihydroneopterin aldolase from Bacillus subtilis (NCBI Identifier No. gi 141435). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Bacillus subtilis Dihydroneopterin Aldolase

| Clone | Status | BLAST pLog Score to (gi 141435) |
| --- | --- | --- |
| ccoln.pk075.j3 | (FIS) | 21.70 |
| sdp3c.pk002.o16 | (FIS) | 20.70 |
| wdk1c.pk013.k22 | (FIS) | 22.04 |

The data in Table 4 represents a calculation of the percent identity of the amino acid sequences set forth in SEQ ID NOs:2, 4 and 6 and the Bacillus subtilis sequence.

TABLE 4

Percent Identity of Amino Acid Sequences Deduced From the Nucleotide Sequences of cDNA Clones Encoding Polypeptides Homologous to Bacillus subtilis Dihydroneopterin Aldolase

| SEQ ID NO. | Percent Identity to |
| --- | --- |
| 2 | 41% (gi 141435) |
| 4 | 33% (gi 141435) |
| 6 | 41% (gi 141435) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a dihydroneopterin aldolase. These sequences represent the first corn, soybean and wheat sequences encoding dihydroneopterin aldolase.

Example 4

Characterization of cDNA Clones Encoding Dihydropteroate Synthase/Dihydropteroate Pyrophosphorylase The BLASTX search using the EST sequences from clones listed in Table 5 revealed similarity of the polypeptides encoded by the cDNAs to dihydropteroate synthase/dihydropteroate pyrophosphorylase from *Pisum sativum* (NCBI Identifier No. gi 1934972) and *Arabidopsis thaliana* (NCBI Identifier No. gi 4938476). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to *Pisum sativum* and *Arabidopsis thaliana* Dihydropteroate Synthase/Dihydropteroate Pyrophosphorylase

| Clone | Status | BLAST pLog Score |
|---|---|---|
| cr1n.pk0057.a10 | FIS | 157.00 (gi 1934972) |
| r10n.pk0041.c3 | FIS | 20.52 (gi 4938476) |
| sdp4c.pk034.b11 | FIS | 57.30 (gi 1934972) |

The data in Table 6 represents a calculation of the percent identity of the amino acid sequences set forth in SEQ ID NOs:8, 10 and 12 and the *Pisum sativum* and *Arabidopsis thaliana* sequences.

TABLE 6

Percent Identity of Amino Acid Sequences Deduced From the Nucleotide Sequences of cDNA Clones Encoding Polypeptides Homologous to *Pisum sativum* and *Arabidopsis thaliana* Dihydropteroate Synthase/Dihydropteroate Pyrophosphorylase

| SEQ ID NO. | Percent Identity to |
|---|---|
| 8 | 58% (gi 1934972) |
| 10 | 59% (gi 4938476) |
| 12 | 71% (gi 1934972) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a dihydropteroate synthase/dihydropteroate pyrophosphorylase. These sequences represent the first corn, rice and soybean sequences encoding dihydropteroate synthase/dihydropteroate pyrophosphorylase.

Example 5

Characterization of cDNA Clones Encoding Tetrahydrofolypolyglutamate Synthase/Folylpolyglutamate Synthase The BLASTX search using the EST sequences from clones listed in Table 7 revealed similarity of the polypeptides encoded by the cDNAs to tetrahydrofolypolyglutamate synthase/folylpolyglutamate synthase from *Arabidopsis thaliana* (NCBI Identifier No. gi 6143861), *Homo sapiens* (NCBI Identifier No. gi 4826728) and *Homo sapiens* (NCBI Identifier No. gi 1709377). Shown in Table 7 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 7

BLAST Results for Sequences Encoding Polypeptides Homologous to *Arabidopsis thaliana* and *Homo sapiens* Tetrahydrofolypolyglutamate Synthase/Folylpolyglutamate Synthase

| Clone | Status | BLAST pLog Score |
|---|---|---|
| cco1n.pk061.116 | FIS | 116.00 (gi 6143861) |
| p0006.cbysj94r | EST | 7.52 (gi 1709377) |
| s12.pk123.k13 | EST | 31.70 (gi 6143861) |

The data in Table 8 represents a calculation of the percent identity of the amino acid sequences set forth in SEQ ID NOs: 14, 16 and 18 and the *Arabidopsis thaliana* and *Homo sapiens* sequences.

TABLE 8

Percent Identity of Amino Acid Sequences Deduced From the Nucleotide Sequences of cDNA Clones Encoding Polypeptides Homologous to *Arabidopsis thaliana* and *Homo sapiens* Tetrahydrofolypolyglutamate Synthase/Folylpolyglutamate Synthase

| SEQ ID NO. | Percent Identity to |
|---|---|
| 14 | 46% (gi 6143861) |
| 16 | 21% (gi 1709377) |
| 18 | 37% (gi 6143861) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a tetrahydrofolypolyglutamate synthase/folylpolyglutamate synthase. These sequences represent the first corn, rice and soybean sequences encoding tetrahydrofolypolyglutamate synthase/folylpolyglutamate synthase.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarosesolidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 9

Evaluating Compounds for Their Ability to Inhibit the Activity of Folate Biosynthetic Enzymes The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for dihydroneopterin aldolase are presented by Hennig et al. 1998 *Nat. Struct. Biol.* 5(5):357–362. Assays for dihydropteroate synthase/dihydropteroate pyrophosphorylase are presented by Rebeile et al. *EMBO J.* 16(5):947–957 and tetrahydrofolypolyglutamate synthase/folylpolyglutamate synthase are presented by Shane et al. 1987 *Biochemistry* 26(2):504–512.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having tetrahydrofolylpolyglutamate synthase/folylpolyglutamate synthase activity, wherein the amino acid sequence of the polypeptide and the amino acid sequence of SEQ ID NO:14 have at least 80% sequence identity based on the Clustal alignment method, or
   (b) the complement of the nucleotide sequence.

2. The polynucleotide of claim 1, wherein the amino acid sequence of the polypeptide and the amino acid sequence of SEQ ID NO:14 have at least 85% sequence identity based on the Clustal alignment method.

3. The polynucleotide of claim 1, wherein the amino acid sequence of the polypeptide and the amino acid sequence of SEQ ID NO:14 have at least 90% sequence identity based on the Clustal alignment method.

4. The polynucleotide of claim 1, wherein the amino acid sequence of the polypeptide and the amino acid sequence of SEQ ID NO:14 have at least 95% sequence identity based on the Clustal alignment method.

5. The polynucleotide of claim 1, wherein the nucleotide sequence comprises the nucleotide sequence of SEQ ID NO:13.

6. The polynucleotide of claim 1, wherein the polypeptide comprises the amino acid sequence of SEQ ID NO:14.

7. A recombinant DNA construct comprising the polynucleotide of claim 1 operably linked to a regulatory sequence.

8. A method for transforming a cell comprising transforming a cell with the polynucleotide of claim 1.

9. A cell comprising the recombinant DNA construct of claim 7.

10. A method for producing a plant comprising transforming a plant cell with the polynucleotide of claim 1 and regenerating a plant from the transformed plant cell.

11. A plant comprising the recombinant DNA construct of claim 7.

12. A seed comprising the recombinant DNA construct of claim 7.

* * * * *

SEQUENCE LISTING

<160> NUMBER OF SEQ ID NOS: 32

<210> SEQ ID NO 1
<211> LENGTH: 658
<212> TYPE: DNA
<213> ORGANISM: Zea mays

<400> SEQUENCE: 1

```
gcacgagggc ggcggctacg tggggtggcg acgacaagct cattctgcgc ggccttcagt      60
tccatggctt ccacggtgtc ctgcaggagg agaagacgtt gggacagaag ttcgtggttg     120
acatcgacgc ctggatagac ctcgccgctg ccggcgagtc cgactgcatt gctgacaccg     180
tcagctacac cgatatctac agcattgcaa aggatgttgt cgagggcacg ccacgcaacc     240
tcttggagtc ggtagctcac tcgatcgcag aggccacgct gctcaagttc cctcagatct     300
```

```
ccgcagtccg agtgaaggtt ggcaagcctc acgtcgcggt gcgaggcgtt ctggactacc      360
tgggcgtgga gataacgagg cacagaaaga agaatgaga tgctgtacac atgtggtgat       420
ggggagccag ttcaatgctg atggcactgc ggccataacc ataatccacg cacgcttgtt      480
gcttgttggc aactaggcat atcccttta cctctgaact gttggaatat cgggaatctg       540
ttcccctagt tgctttatta cgaattcaga tcatatctgg ctagtaagat caaccttctt     600
ctggtctgta acaaaaaaaa aaaaaaaaa aaaaaaaaa aaaaaaaaa aaaaaaa            658
```

<210> SEQ ID NO 2
<211> LENGTH: 131
<212> TYPE: PRT
<213> ORGANISM: Zea mays

<400> SEQUENCE: 2

```
Thr Arg Ala Ala Ala Thr Trp Gly Gly Asp Asp Lys Leu Ile Leu Arg
  1               5                  10                  15

Gly Leu Gln Phe His Gly Phe His Gly Val Leu Gln Glu Glu Lys Thr
             20                  25                  30

Leu Gly Gln Lys Phe Val Val Asp Ile Asp Ala Trp Ile Asp Leu Ala
         35                  40                  45

Ala Ala Gly Glu Ser Asp Cys Ile Ala Asp Thr Val Ser Tyr Thr Asp
     50                  55                  60

Ile Tyr Ser Ile Ala Lys Asp Val Val Glu Gly Thr Pro Arg Asn Leu
 65                  70                  75                  80

Leu Glu Ser Val Ala His Ser Ile Ala Glu Ala Thr Leu Leu Lys Phe
                 85                  90                  95

Pro Gln Ile Ser Ala Val Arg Val Lys Val Gly Lys Pro His Val Ala
            100                 105                 110

Val Arg Gly Val Leu Asp Tyr Leu Gly Val Glu Ile Thr Arg His Arg
        115                 120                 125

Lys Lys Glu
    130
```

<210> SEQ ID NO 3
<211> LENGTH: 705
<212> TYPE: DNA
<213> ORGANISM: Glycine max

<400> SEQUENCE: 3

```
gcacgagcgg agaggcgagg gagtgaggga ctagcacaga aagatattgt ttggtgtacg       60
gtggtgagtg tcgacgctgc cactctcgcc tgtgtctgtg ataaatggaa tctgatgcac     120
cgacatgggg agacaaactc atgttgaggg gattgtcatt ccatggtttt catggagcaa     180
agcctgaaga aaggacactg gccagaagt tcttcataga tatagatgct tggatggatc      240
tcaaagcagc tggcaaatct gatcactat cagattctgt tagttacaca gaaatatatg      300
atatagctaa ggatgttctt gaagggtcac ctcacaatct tctggagtca gtggcccaaa     360
aaattgcaat cactactctt acaaatcata agaaatatc tgctgtccga gtgaaggttg      420
gaaagcctca tgtggcagtt cggggtccag ttgattactt aggcgttgag attcttagac     480
gcagaagcga cttgtcaggc tagaaattc atatttattg ctgcacaatt tttatatttt      540
cacattccac ttgatacaaa agtaatgtaa ctctttcctt catgccccat tagtcttttc     600
tctcttaagc aatcttgcta atgaaattaa aagatcaaag ttaggcatat taaaggaact    660
atacaattaa tttggattct ccaaaacaaa aaaaaaaaaa aaaaa                    705
```

<210> SEQ ID NO 4
<211> LENGTH: 132
<212> TYPE: PRT
<213> ORGANISM: Glycine max

<400> SEQUENCE: 4

Met Glu Ser Asp Ala Pro Thr Trp Gly Asp Lys Leu Met Leu Arg Gly
 1               5                  10                  15

Leu Ser Phe His Gly Phe His Gly Ala Lys Pro Glu Glu Arg Thr Leu
            20                  25                  30

Gly Gln Lys Phe Phe Ile Asp Ile Asp Ala Trp Met Asp Leu Lys Ala
        35                  40                  45

Ala Gly Lys Ser Asp His Leu Ser Asp Ser Val Ser Tyr Thr Glu Ile
    50                  55                  60

Tyr Asp Ile Ala Lys Asp Val Leu Glu Gly Ser Pro His Asn Leu Leu
65                  70                  75                  80

Glu Ser Val Ala Gln Lys Ile Ala Ile Thr Thr Leu Thr Asn His Lys
                85                  90                  95

Glu Ile Ser Ala Val Arg Val Lys Val Gly Lys Pro His Val Ala Val
            100                 105                 110

Arg Gly Pro Val Asp Tyr Leu Gly Val Glu Ile Leu Arg Arg Arg Ser
        115                 120                 125

Asp Leu Ser Gly
    130

<210> SEQ ID NO 5
<211> LENGTH: 759
<212> TYPE: DNA
<213> ORGANISM: Triticum aestivum

<400> SEQUENCE: 5
gcacgagcca ggttccactc cacccaccca cctgcgccgc cagctctaaa ggaggcggcg      60
tcggccggcg gcgagcgca cgcccaggcc aatcgatcg atcccagctc tagaggggag     120
ggagcaacca tggcgggga cggggaggac gaggtgccgg cgatgggcgg agacaagctg     180
atcctgcggg gctgcagtt ccacggcttc cacggcgtga agcaggagga gaagaagctg     240
ggccagaagt tcgtggtcga cgtggacgcc tggatggacc tcgccgccgc cggggactcc     300
gacgacatcg cccacaccgt cagctacacc gacatctaca ggatagccaa gggcgtggtg     360
gaaggcccgt cgcggaacct cctggagtcg gtggcgcagt cgatcgccgg caccacgctg     420
ctcgagtttc cccagatctc cgccgtccgg gtgaaggtcg ggaagcccca cgtcgcggtg     480
cagggcgtcg tcgactacct cggggtggag atactgagga ggcgcagaga ggcatgagca     540
caagaaccgg agtacctcat atgagaagcc tgaacagagt tgatctcagt tgagcccatc     600
gatccctgtg tcttatatct atcaatctat gtatgtatgg acatgatgtt tgtctgcgct     660
caataatttc tgaattggga atcatgttct tgccaaaaaa aaaaaaaaaa aaaaaaaaa     720 aaaaaaaaa aaaaaaaaa aaaaaaaaa aaaaaaaa                               759

<210> SEQ ID NO 6
<211> LENGTH: 178
<212> TYPE: PRT
<213> ORGANISM: Triticum aestivum

<400> SEQUENCE: 6

Ala Arg Ala Arg Phe His Ser Thr His Pro Ala Pro Pro Ala Leu
 1               5                  10                  15

-continued

```
Lys Glu Ala Ala Ser Ala Gly Gly Arg Ala His Ala Gln Ala Gln Ser
                 20                  25                  30

Ile Asp Pro Ser Ser Arg Gly Glu Gly Ala Thr Met Ala Gly Asp Gly
             35                  40                  45

Glu Asp Glu Val Pro Ala Met Gly Gly Asp Lys Leu Ile Leu Arg Gly
         50                  55                  60

Leu Gln Phe His Gly Phe His Gly Val Lys Gln Glu Lys Lys Leu
 65                  70                  75                  80

Gly Gln Lys Phe Val Asp Val Asp Ala Trp Met Asp Leu Ala Ala
                 85                  90                  95

Ala Gly Asp Ser Asp Asp Ile Ala His Thr Val Ser Tyr Thr Asp Ile
            100                 105                 110

Tyr Arg Ile Ala Lys Gly Val Val Glu Gly Pro Ser Arg Asn Leu Leu
            115                 120                 125

Glu Ser Val Ala Gln Ser Ile Ala Gly Thr Thr Leu Leu Glu Phe Pro
        130                 135                 140

Gln Ile Ser Ala Val Arg Val Lys Val Gly Lys Pro His Val Ala Val
145                 150                 155                 160

Gln Gly Val Val Asp Tyr Leu Gly Val Glu Ile Leu Arg Arg Arg
                165                 170                 175

Glu Ala

<210> SEQ ID NO 7
<211> LENGTH: 1824
<212> TYPE: DNA
<213> ORGANISM: Zea mays

<400> SEQUENCE: 7
gcacgagcct cgaacgaggg ccgtacctag cgcctctgtc cttcgtcggc cgtcgcactg      60
tgctcccgtc cgcctccggc tccgccaac ccgcgtccgc ccacgactag gcggtctgg      120 gcaggtcctt ccacaaagat gtgaaggatt aaagctcatg tgaaagattc taagactaca     180
attggtatca agcggttgct ttcttatttc tcatacgctc aaccatgctc ctgcatgcta     240
aggattcagt taggaagatg cattcagttg ctaagaacta cttttgtgtct gatcttactc    300 atcctccaag atccttgaac agagcttcca gacatgttgt tccattcaag acccgttct     360 ttacgcattg ctcacttgag agccgttcag ttgaccaaga gattgtgatt gctatgggaa    420
gcaatgtagg cgatagagtc agtacattca acagggcatt gcagctgatg aaaagctctg    480
acgtgaacat cactaggcat gcctgtctct atgagaccgc ccctgcttat ttgactgatc    540
agccgcggtt tcttaactct gccattcggg gcacaactag gctcaggcca catgagcttc    600
ttaaactgct aaaggaaatt gagaaggata ttggccgcac tggcggaata aggtgcatct    660
agtgacaacg gtatcgaaac aagttggcac tctctctcaa agtgtagtgg aggtttcttt    720
gagttatgga ataaccttgg gggtgaatct ataattggaa cagaaagcat taaagggta    780 ttacctgttg gggatcgttt gttggattgg tgtgagagga ctcttgtcat ggggtcctt    840 aatttgacac cagacagctt tagtgatgga ggtaagtttc tagaagtggg agctgccatt    900
tctcaggcta agtcattaat ctcagaaggt gcagatatca ttgatattgg tgctcaatct    960
accaggccct ttgcaaaaag attatctcca aatgaggagc ttgagaggtt ggttcctgtt   1020
ctggatgaga ttcaaaaat ccctgagatg gagggcaagt tactctcagt ggatacattc   1080
tatgcagaag ttgccagtga agctgtgaaa agaggagctc acatgatcaa cgatgtatcc   1140
```

-continued

```
agtggacagc ttgatccaat aattcttaaa gtggcagctg aacttggagt tccatatgtt    1200
gcaatgcaca tgaggggaga tccgtcaact atgcaaagcg aacaaaatgt tcactatgat    1260
aatgtctgca aggaagttgc tttggagcta tacacacagg tgagagaagc agagttatct    1320
gggattccat tgtggaggct ggttcttgat cctggcattg gcttctccaa gaaatctgaa    1380
cataaccttg aagtaattat gggattggaa tccattagga gggagatggg taaaatgagt    1440
ataggtgctt cacatgtgcc aatattactg ggaccttcaa ggaaaagctt tttgggtgaa    1500
atatgcaatc gtgccaatcc agttgagaga gatgttgcta ctgttgcagc cgtgacagct    1560
gggattttga atggtgctaa cattgtaaga gtccataatg ctggatatgg tgtagacgcc    1620
gcaaaggttt gtgatgcatt gcgtaagcgt aagggaagtt gcagaaactg aactatcgct    1680
ccagttttat acaagaaaaa agtgatgtcg aaaaatgtga tttgtgaagt atcgttgttg    1740
taatgaacca gagataatgc ttttcttgt gtcaccaagg aataaagtca gaagctgct    1800 actcaaaaaa aaaaaaaaaa aaaa                                          1824
```

<210> SEQ ID NO 8
<211> LENGTH: 481
<212> TYPE: PRT
<213> ORGANISM: Zea mays

<400> SEQUENCE: 8

```
Met Leu Leu His Ala Lys Asp Ser Val Arg Lys Met His Ser Val Ala
  1               5                  10                  15

Lys Asn Tyr Phe Val Ser Asp Leu Thr His Pro Arg Ser Leu Asn
             20                  25                  30

Arg Ala Ser Arg His Val Val Pro Phe Lys Thr Arg Phe Phe Thr His
         35                  40                  45

Cys Ser Leu Glu Ser Arg Ser Val Asp Gln Glu Ile Val Ile Ala Met
     50                  55                  60

Gly Ser Asn Val Gly Asp Arg Val Ser Thr Phe Asn Arg Ala Leu Gln
 65                  70                  75                  80

Leu Met Lys Ser Ser Asp Val Asn Ile Thr Arg His Ala Cys Leu Tyr
                 85                  90                  95

Glu Thr Ala Pro Ala Tyr Leu Thr Asp Gln Pro Arg Phe Leu Asn Ser
            100                 105                 110

Ala Ile Arg Gly Thr Thr Arg Leu Arg Pro His Glu Leu Leu Lys Leu
        115                 120                 125

Leu Lys Glu Ile Glu Lys Asp Ile Gly Arg Thr Gly Ile Arg Cys
    130                 135                 140

Thr Ser Asp Asn Gly Ile Glu Thr Ser Trp His Ser Leu Ser Lys Cys
145                 150                 155                 160

Ser Gly Gly Phe Phe Glu Leu Trp Asn Asn Leu Gly Gly Glu Ser Ile
                165                 170                 175

Ile Gly Thr Glu Ser Ile Lys Arg Val Leu Pro Val Gly Asp Arg Leu
            180                 185                 190

Leu Asp Trp Cys Glu Arg Thr Leu Val Met Gly Val Leu Asn Leu Thr
        195                 200                 205

Pro Asp Ser Phe Ser Asp Gly Gly Lys Phe Leu Glu Val Gly Ala Ala
    210                 215                 220

Ile Ser Gln Ala Lys Ser Leu Ile Ser Glu Gly Ala Asp Ile Ile Asp
225                 230                 235                 240

Ile Gly Ala Gln Ser Thr Arg Pro Phe Ala Lys Arg Leu Ser Pro Asn
                245                 250                 255
```

Glu Glu Leu Glu Arg Leu Val Pro Val Leu Asp Glu Ile Thr Lys Ile
            260                 265                 270

Pro Glu Met Glu Gly Lys Leu Leu Ser Val Asp Thr Phe Tyr Ala Glu
            275                 280                 285

Val Ala Ser Glu Ala Val Lys Arg Gly Ala His Met Ile Asn Asp Val
            290                 295                 300

Ser Ser Gly Gln Leu Asp Pro Ile Ile Leu Lys Val Ala Ala Glu Leu
305                 310                 315                 320

Gly Val Pro Tyr Val Ala Met His Met Arg Gly Asp Pro Ser Thr Met
                    325                 330                 335

Gln Ser Glu Gln Asn Val His Tyr Asp Asn Val Cys Lys Glu Val Ala
            340                 345                 350

Leu Glu Leu Tyr Thr Gln Val Arg Glu Ala Glu Leu Ser Gly Ile Pro
            355                 360                 365

Leu Trp Arg Leu Val Leu Asp Pro Gly Ile Gly Phe Ser Lys Lys Ser
            370                 375                 380

Glu His Asn Leu Glu Val Ile Met Gly Leu Glu Ser Ile Arg Arg Glu
385                 390                 395                 400

Met Gly Lys Met Ser Ile Gly Ala Ser His Val Pro Ile Leu Leu Gly
                    405                 410                 415

Pro Ser Arg Lys Ser Phe Leu Gly Glu Ile Cys Asn Arg Ala Asn Pro
            420                 425                 430

Val Glu Arg Asp Val Ala Thr Val Ala Ala Val Thr Ala Gly Ile Leu
            435                 440                 445

Asn Gly Ala Asn Ile Val Arg Val His Asn Ala Gly Tyr Gly Val Asp
            450                 455                 460

Ala Ala Lys Val Cys Asp Ala Leu Arg Lys Arg Lys Gly Ser Cys Arg
465                 470                 475                 480

Asn

<210> SEQ ID NO 9
<211> LENGTH: 589
<212> TYPE: DNA
<213> ORGANISM: Oryza sativa

<400> SEQUENCE: 9
gcacgagctt acagtttagg tgcttcacat gtgccaattt tacttggacc ctcaaggaaa      60
agatttttag gtgaaatatg caatcgtgtc aatcccactg agagagatgc tgctaccatg     120
gtcgttgcta ctgctgggat attgaatggt gctaatatag taagggtgca taatgttaaa     180
tatggcgtgg atactgcaaa ggtctctgat gcattgagca aaggcagaag atgattatac     240
caccttcgga aaatagatca tactccagtt ttgtactaga aaataatgat caataatagt     300
aactcggcca taatgttggc ttctcagata ataccatagg gcgagtatca tcatagaaag     360
catgtgcaca caactgttat gtgagcttga gatggaattt ttcttttgt cacatcattt     420
caataatctt ctgaggtaac ggttatacag atctctagag ttttgacctt tcaggattca     480
caaattttct acaggtctga tttgtttgga actttgggcc ataacttgaa gttattctcc     540
atgtaaaaaa aaaaaaaaaa aaaaaaaaaa aaaaaaaaaa aaaaaaaaa                 589

<210> SEQ ID NO 10
<211> LENGTH: 75
<212> TYPE: PRT
<213> ORGANISM: Oryza sativa

```
<400> SEQUENCE: 10

Ala Arg Ala Tyr Ser Leu Gly Ala Ser His Val Pro Ile Leu Leu Gly
 1               5                  10                  15

Pro Ser Arg Lys Arg Phe Leu Gly Glu Ile Cys Asn Arg Val Asn Pro
            20                  25                  30

Thr Glu Arg Asp Ala Ala Thr Met Val Val Ala Thr Ala Gly Ile Leu
        35                  40                  45

Asn Gly Ala Asn Ile Val Arg Val His Asn Val Lys Tyr Gly Val Asp
    50                  55                  60

Thr Ala Lys Val Ser Asp Ala Leu Ser Lys Gly
65                  70                  75

<210> SEQ ID NO 11
<211> LENGTH: 493
<212> TYPE: DNA
<213> ORGANISM: Glycine max
<220> FEATURE:
<221> NAME/KEY: unsure
<222> LOCATION: (376)..(377)
<220> FEATURE:
<221> NAME/KEY: unsure
<222> LOCATION: (421)
<220> FEATURE:
<221> NAME/KEY: unsure
<222> LOCATION: (441)..(442)..(443)
<220> FEATURE:
<221> NAME/KEY: unsure
<222> LOCATION: (456)
<220> FEATURE:
<221> NAME/KEY: unsure
<222> LOCATION: (458)
<220> FEATURE:
<221> NAME/KEY: unsure
<222> LOCATION: (462)
<220> FEATURE:
<221> NAME/KEY: unsure
<222> LOCATION: (467)
<220> FEATURE:
<221> NAME/KEY: unsure
<222> LOCATION: (473)..(474)
<220> FEATURE:
<221> NAME/KEY: unsure
<222> LOCATION: (477)
<220> FEATURE:
<221> NAME/KEY: unsure
<222> LOCATION: (485)
<220> FEATURE:
<221> NAME/KEY: unsure
<222> LOCATION: (491)

<400> SEQUENCE: 11
cttgactggt cgcggagaac ttccgtcatg gggatcctta atgtgactcc agatagtttt      60
agtgatgggg gaaatttcaa gtctgtggag tctgctgttt atcaggttcg gttaatgatt     120
tcagaaggag cagatatgat tgatatcggg gctcagtcta ctcggccaac ggcctctagg     180
atctctgctg cagaagaatt aggtagatta atccctgtcc tggaagctgt agtgtcaatg     240
cctgaggtag aaggaaagct catttctgtg gatactttct actctgaagt tgcttcacaa     300
gcagtgagta aagggctca tcttataaat gatgtatcct gcctggacag ttggatagta     360
acatgtttaa agtccnnggg ctggatcttg atgttcttaa tgttgcaaat ggcacaatga     420
nggggggaac catccttaca nnngcaagaa taagtngnaa antctgnaaa tanngnaat     480 tgttntgtta naa                                                       493

<210> SEQ ID NO 12
<211> LENGTH: 139
```

<212> TYPE: PRT
<213> ORGANISM: Glycine max
<220> FEATURE:
<221> NAME/KEY: UNSURE
<222> LOCATION: (126)

<400> SEQUENCE: 12

Leu Asp Trp Ser Arg Arg Thr Ser Val Met Gly Ile Leu Asn Val Thr
1               5                   10                  15

Pro Asp Ser Phe Ser Asp Gly Gly Asn Phe Lys Ser Val Glu Ser Ala
            20                  25                  30

Val Tyr Gln Val Arg Leu Met Ile Ser Glu Gly Ala Asp Met Ile Asp
        35                  40                  45

Ile Gly Ala Gln Ser Thr Arg Pro Thr Ala Ser Arg Ile Ser Ala Ala
    50                  55                  60

Glu Glu Leu Gly Arg Leu Ile Pro Val Leu Glu Ala Val Val Ser Met
65                  70                  75                  80

Pro Glu Val Glu Gly Lys Leu Ile Ser Val Asp Thr Phe Tyr Ser Glu
                85                  90                  95

Val Ala Ser Gln Ala Val Ser Lys Gly Ala His Leu Ile Asn Asp Val
            100                 105                 110

Ser Cys Leu Asp Ser Trp Ile Val Thr Cys Leu Lys Ser Xaa Gly Trp
        115                 120                 125

Ile Leu Met Phe Leu Met Leu Gln Met Ala Gln
    130                 135

<210> SEQ ID NO 13
<211> LENGTH: 2041
<212> TYPE: DNA
<213> ORGANISM: Zea mays

<400> SEQUENCE: 13
gcacgagccc tcgcctgctc cacgacgctt atgcgctcgc gtcccgctct cgccgcccac      60
ctccggcgcc tgctcctcct ctctcccctcc gcccacctca tcatcatccg ccgcgccatg    120
gcatccgccg ccgccgcgca ggcgcagcca ggtggcgccc cgccggcgac cgcggagtac     180
gaggaggtgc tggggcggct ctcctcgctc atcacgcaga aggtgcgcgc gaacagcgcc     240
aaccgcggca accagtggga cctcatggag cactacgtca agattctgga gctggaggag     300
tcgatcgcgc ggatgaaagt gattcacgtc gcgggggacca aggggaaggg ttccacatgc    360
acattcaccg agtcaatcct gcgatcgtgt ggcttccata ctgggctgtt cacctcacca    420
catttgatgg atgttagaga gcgatttcag ctagatgggg ttaatatttc tgaagagaaa    480
tttttgaagt acttctggtg gtgctggaac aagttgaagg agaagactga tgatgatatt    540
cccatgccag cctatttcag gttcctcgcg ttgctcgcat tcaagatatt ttctgctgag    600
caggtagatg ttgctgttct cgaggttggc ctaggaggga gtttgatgc aactaatgtg      660
gttaaagcac ctgtagtttg tggcatatct tcccttggat atgatcatat ggaaattctt    720
gggaatacac ttgagaaaat cgcaggagag aaggctggga ttttcaagaa aggagttccg    780
gcctatactg ctccacaacc agaagaggca atgactgctc tcaaacaaag agcttcggaa    840
ttgggtatct ctctccaagt cgttgatcct tggagcccc atcacctaaa agatcagcat     900
cttgggctgc atggagaaca tcaatatata aatgctggcc ttgcagttgc tttggctagt    960
acgtggcttg agaagcaggg acataaagat acgttaccac tcaatcgtac tgatcccttta   1020
ccagatcatt ttattagagg gctatcaagt gcttctttgc aaggccgagc acagattgtt   1080

-continued

```
ccagattcac aagtgaattc agaagagaag gacaaaaatt gttctcttgt tttttatttg      1140
gatggagcgc acagtcctga aagcatggaa gtatgtggca agtggttttc ccatgtcaca      1200
aaggatgata caaggctacc atcttctgtg gagcagtctc atacatctat gtctcaaaag      1260
atccttctgt tcaactgcat gtctgtgaga gatccgatga gattgcttcc ttgtctcctg      1320
gatgcatcaa ctcaaaatgg agtccacttt gacctggccc tatttgtgcc gaaccaatca      1380
caacacacga agcttggttc taacacttca gcaccagcgg agcctgagca aatcgatttg      1440
tcatggcagc tgtcacttca aacagtgtgg gagaagttac ttcaggataa aggtataaat      1500
actacaaaat ccagtgatac tagtaaagtt tttgattcgc ttccaatcgc aatcgagtgg      1560
ctaaggagaa atgcccgaga aaaccaatct acttctttcc aggtgctggt tactggctcc      1620
ctgcatctcg ttggggatgt cttgagaata atcaagaagt gatacgccgc ctcgaaatcc      1680
aaactggaac tggactatga tctatggtct ctcccaaggc taacatgatt agcaagggga      1740
gacatttgaa cggtgcttgc ttattggtgc caaccaagct gcgagcttct tgtgtttttt      1800
ttgtgtggcc acggtcgcct gcctaccact cgggaaaccg ccgcgcccgt tcttgtgaag      1860
gcatgaaata ggatgatcgt gccaccatag aacataactg ggaaatgaat tcgacatgga      1920
actgggacag tctgtatact cacaaaataa gatcgcatgg ggttttcttg ttcaagtgca      1980
aagaaaccag tcaattctta tccagagtag caagaattca ttcaaaaaaa aaaaaaaaa      2040 a                                                                      2041
```

<210> SEQ ID NO 14
<211> LENGTH: 553
<212> TYPE: PRT
<213> ORGANISM: Zea mays

<400> SEQUENCE: 14

```
Ala Arg Ala Leu Ala Cys Ser Thr Thr Leu Met Arg Ser Arg Pro Ala
  1               5                  10                  15

Leu Ala Ala His Leu Arg Arg Leu Leu Leu Ser Pro Ser Ala His
             20                  25                  30

Leu Ile Ile Ile Arg Arg Ala Met Ala Ser Ala Ala Ala Gln Ala
         35                  40                  45

Gln Pro Gly Gly Ala Pro Pro Ala Thr Ala Glu Tyr Glu Glu Val Leu
     50                  55                  60

Gly Arg Leu Ser Ser Leu Ile Thr Gln Lys Val Arg Ala Asn Ser Ala
 65                  70                  75                  80

Asn Arg Gly Asn Gln Trp Asp Leu Met Glu His Tyr Val Lys Ile Leu
                 85                  90                  95

Glu Leu Glu Glu Ser Ile Ala Arg Met Lys Val Ile His Val Ala Gly
            100                 105                 110

Thr Lys Gly Lys Gly Ser Thr Cys Thr Phe Thr Glu Ser Ile Leu Arg
        115                 120                 125

Ser Cys Gly Phe His Thr Gly Leu Phe Thr Ser Pro His Leu Met Asp
    130                 135                 140

Val Arg Glu Arg Phe Gln Leu Asp Gly Val Asn Ile Ser Glu Glu Lys
145                 150                 155                 160

Phe Leu Lys Tyr Phe Trp Trp Cys Trp Asn Lys Leu Lys Glu Lys Thr
                165                 170                 175

Asp Asp Asp Ile Pro Met Pro Ala Tyr Phe Arg Phe Leu Ala Leu Leu
            180                 185                 190

Ala Phe Lys Ile Phe Ser Ala Glu Gln Val Asp Val Ala Val Leu Glu
```

-continued

```
            195                 200                 205
Val Gly Leu Gly Gly Lys Phe Asp Ala Thr Asn Val Val Lys Ala Pro
            210                 215                 220
Val Val Cys Gly Ile Ser Ser Leu Gly Tyr Asp His Met Glu Ile Leu
225                 230                 235                 240
Gly Asn Thr Leu Gly Glu Ile Ala Gly Glu Lys Ala Gly Ile Phe Lys
            245                 250                 255
Lys Gly Val Pro Ala Tyr Thr Ala Pro Gln Pro Glu Glu Ala Met Thr
            260                 265                 270
Ala Leu Lys Gln Arg Ala Ser Glu Leu Gly Ile Ser Leu Gln Val Val
            275                 280                 285
Asp Pro Leu Glu Pro His His Leu Lys Asp Gln His Leu Gly Leu His
            290                 295                 300
Gly Glu His Gln Tyr Ile Asn Ala Gly Leu Ala Val Ala Leu Ala Ser
305                 310                 315                 320
Thr Trp Leu Glu Lys Gln Gly His Lys Asp Thr Leu Pro Leu Asn Arg
            325                 330                 335
Thr Asp Pro Leu Pro Asp His Phe Ile Arg Gly Leu Ser Ser Ala Ser
            340                 345                 350
Leu Gln Gly Arg Ala Gln Ile Val Pro Asp Ser Gln Val Asn Ser Glu
            355                 360                 365
Glu Lys Asp Lys Asn Cys Ser Leu Val Phe Tyr Leu Asp Gly Ala His
            370                 375                 380
Ser Pro Glu Ser Met Glu Val Cys Gly Lys Trp Phe Ser His Val Thr
385                 390                 395                 400
Lys Asp Asp Thr Arg Leu Pro Ser Ser Val Glu Gln Ser His Thr Ser
            405                 410                 415
Met Ser Gln Lys Ile Leu Leu Phe Asn Cys Met Ser Val Arg Asp Pro
            420                 425                 430
Met Arg Leu Leu Pro Cys Leu Leu Asp Ala Ser Thr Gln Asn Gly Val
            435                 440                 445
His Phe Asp Leu Ala Leu Phe Val Pro Asn Gln Ser Gln His Thr Lys
            450                 455                 460
Leu Gly Ser Asn Thr Ser Ala Pro Ala Glu Pro Glu Gln Ile Asp Leu
465                 470                 475                 480
Ser Trp Gln Leu Ser Leu Gln Thr Val Trp Glu Lys Leu Leu Gln Asp
            485                 490                 495
Lys Gly Ile Asn Thr Thr Lys Ser Ser Asp Thr Ser Lys Val Phe Asp
            500                 505                 510
Ser Leu Pro Ile Ala Ile Glu Trp Leu Arg Arg Asn Ala Arg Glu Asn
            515                 520                 525
Gln Ser Thr Ser Phe Gln Val Leu Val Thr Gly Ser Leu His Leu Val
            530                 535                 540
Gly Asp Val Leu Arg Ile Ile Lys Lys
545                 550

<210> SEQ ID NO 15
<211> LENGTH: 534
<212> TYPE: DNA
<213> ORGANISM: Zea mays
<220> FEATURE:
<221> NAME/KEY: unsure
<222> LOCATION: (8)
<220> FEATURE:
<221> NAME/KEY: unsure
<222> LOCATION: (14)..(15)
```

<220> FEATURE:
<221> NAME/KEY: unsure
<222> LOCATION: (26)
<220> FEATURE:
<221> NAME/KEY: unsure
<222> LOCATION: (49)
<220> FEATURE:
<221> NAME/KEY: unsure
<222> LOCATION: (182)
<220> FEATURE:
<221> NAME/KEY: unsure
<222> LOCATION: (189)
<220> FEATURE:
<221> NAME/KEY: unsure
<222> LOCATION: (271)
<220> FEATURE:
<221> NAME/KEY: unsure
<222> LOCATION: (285)
<220> FEATURE:
<221> NAME/KEY: unsure
<222> LOCATION: (321)..(322)
<220> FEATURE:
<221> NAME/KEY: unsure
<222> LOCATION: (342)
<220> FEATURE:
<221> NAME/KEY: unsure
<222> LOCATION: (413)
<220> FEATURE:
<221> NAME/KEY: unsure
<222> LOCATION: (500)
<220> FEATURE:
<221> NAME/KEY: unsure
<222> LOCATION: (510)
<220> FEATURE:
<221> NAME/KEY: unsure
<222> LOCATION: (512)
<220> FEATURE:
<221> NAME/KEY: unsure
<222> LOCATION: (517)
<220> FEATURE:
<221> NAME/KEY: unsure
<222> LOCATION: (529)

<400> SEQUENCE: 15

```
catggctncc aaannttcgg cactanacgt actgagaaga gctcgcgtnc ccgctactcg      60
ccggcccacc tccgggcgcc tgctcctcct ctctccctcc gcccacctca tcatcatccg     120
ccgcgccatg gcctccgccg ccgccgcgca ggcgcagcag gtggcgcccc accggcgacc     180
gnggagtang aggaggtgct ggggcggctc tcctcgctca tcacgcagaa ggtgcgcgcg     240
aacagcgcca accgcggcaa ccagtgggac ntcatggagc actangtcaa gattctggag     300
ctggaggagt cgatcgcgcg nnatgaaagt gattcacgtc gnagggacca aggggaaggg     360
ttccacatgc acattcaccg agtcaatcct gcgatcgtgt ggcttccata atnggctgtt     420
taactcacca acatttgatt ggatgttaga gagcgaattc agctagattg gggttaataa     480
tttctgaaga gaaattttn aagtactctn gntgtgntgg aacaagttna agga            534
```

<210> SEQ ID NO 16
<211> LENGTH: 154
<212> TYPE: PRT
<213> ORGANISM: Zea mays
<220> FEATURE:
<221> NAME/KEY: UNSURE
<222> LOCATION: (3)
<220> FEATURE:
<221> NAME/KEY: UNSURE
<222> LOCATION: (5)
<220> FEATURE:
<221> NAME/KEY: UNSURE
<222> LOCATION: (9)
<220> FEATURE:
<221> NAME/KEY: UNSURE

```
<222> LOCATION: (61)
<220> FEATURE:
<221> NAME/KEY: UNSURE
<222> LOCATION: (63)
<220> FEATURE:
<221> NAME/KEY: UNSURE
<222> LOCATION: (95)
<220> FEATURE:
<221> NAME/KEY: UNSURE
<222> LOCATION: (107)
<220> FEATURE:
<221> NAME/KEY: UNSURE
<222> LOCATION: (114)
<220> FEATURE:
<221> NAME/KEY: UNSURE
<222> LOCATION: (138)

<400> SEQUENCE: 16
```

Met Ala Xaa Lys Xaa Ser Ala Leu Xaa Val Leu Arg Arg Ala Arg Val
 1               5                  10                  15

Pro Ala Thr Arg Arg Pro Thr Ser Gly Arg Leu Leu Leu Ser Pro
             20                  25                  30

Ser Ala His Leu Ile Ile Ile Arg Arg Ala Met Ala Ser Ala Ala Ala
             35                  40                  45

Ala Gln Ala Gln Gln Val Ala Pro His Arg Arg Pro Xaa Ser Xaa Arg
    50                  55                  60

Arg Cys Trp Gly Gly Ser Pro Arg Ser Ser Arg Arg Cys Ala Arg
65                  70                  75                  80

Thr Ala Pro Thr Ala Ala Thr Ser Gly Thr Ser Trp Ser Thr Xaa Ser
                85                  90                  95

Arg Phe Trp Ser Trp Arg Ser Arg Ser Arg Xaa Met Lys Val Ile His
            100                 105                 110

Val Xaa Gly Thr Lys Gly Lys Gly Ser Thr Cys Thr Phe Thr Glu Ser
        115                 120                 125

Ile Leu Arg Ser Cys Gly Phe His Asn Xaa Leu Phe Asn Ser Pro Thr
        130                 135                 140

Phe Asp Trp Met Leu Glu Ser Glu Phe Ser
145                 150

```
<210> SEQ ID NO 17
<211> LENGTH: 553
<212> TYPE: DNA
<213> ORGANISM: Glycine max
<220> FEATURE:
<221> NAME/KEY: unsure
<222> LOCATION: (520)
<220> FEATURE:
<221> NAME/KEY: unsure
<222> LOCATION: (549)

<400> SEQUENCE: 17
ggcttctcag ttaaatgtac ctcttcaagt ggtaacccca ttagatgcca aattgctaaa      60
tggttcaaga ctagcgcttg gaggtgaaca ccaatatata aatgctggtc ttgctattgc     120
attatgctct acgtggctga aaatgaatgg gcatcttgaa gactcgtact tgaaacatat     180
acaacacact ttaccagaga agttcataaa agggttaaca actgcaagtt tgcaaggaag     240
ggctcagatt gttcctgatc agttcatcaa tgatgaaata ccaaatgaac ttgtcttctt     300
tttagatggg gctcatagtc ctgaaagcat ggaagcatgt gccaggtggt tttctcttgc     360
tattaaagat caagaccaga ttttgtttca tcaagaaact tgataattct aacttctcaa     420
accaagtagt gaagatgcac aatggtgaaa ctgtacagaa gaaatccaca cagattttgc     480
```

```
tgttcaattg tatgtctgag cgaaaccctc aattgcttcn tccccacttg atgaaaacat    540
gtgctgatna agg                                                      553
```

```
<210> SEQ ID NO 18
<211> LENGTH: 133
<212> TYPE: PRT
<213> ORGANISM: Glycine max

<400> SEQUENCE: 18
```

```
Ala Ser Gln Leu Asn Val Pro Leu Gln Val Val Thr Pro Leu Asp Ala
  1               5                  10                  15

Lys Leu Leu Asn Gly Ser Arg Leu Ala Leu Gly Gly Glu His Gln Tyr
             20                  25                  30

Ile Asn Ala Gly Leu Ala Ile Ala Leu Cys Ser Thr Trp Leu Lys Met
         35                  40                  45

Asn Gly His Leu Glu Asp Ser Tyr Leu Lys His Ile Gln His Thr Leu
     50                  55                  60

Pro Glu Lys Phe Ile Lys Gly Leu Thr Thr Ala Ser Leu Gln Gly Arg
 65                  70                  75                  80

Ala Gln Ile Val Pro Asp Gln Phe Ile Asn Asp Glu Ile Pro Asn Glu
                 85                  90                  95

Leu Val Phe Phe Leu Asp Gly Ala His Ser Pro Glu Ser Met Glu Ala
                100                 105                 110

Cys Ala Arg Trp Phe Ser Leu Ala Ile Lys Asp Gln Asp Gln Ile Leu
            115                 120                 125

Phe His Gln Glu Thr
        130
```

```
<210> SEQ ID NO 19
<211> LENGTH: 564
<212> TYPE: DNA
<213> ORGANISM: Zea mays
<220> FEATURE:
<221> NAME/KEY: unsure
<222> LOCATION: (257)
<220> FEATURE:
<221> NAME/KEY: unsure
<222> LOCATION: (371)
<220> FEATURE:
<221> NAME/KEY: unsure
<222> LOCATION: (402)
<220> FEATURE:
<221> NAME/KEY: unsure
<222> LOCATION: (433)
<220> FEATURE:
<221> NAME/KEY: unsure
<222> LOCATION: (441)
<220> FEATURE:
<221> NAME/KEY: unsure
<222> LOCATION: (447)
<220> FEATURE:
<221> NAME/KEY: unsure
<222> LOCATION: (453)
<220> FEATURE:
<221> NAME/KEY: unsure
<222> LOCATION: (468)
<220> FEATURE:
<221> NAME/KEY: unsure
<222> LOCATION: (473)
<220> FEATURE:
<221> NAME/KEY: unsure
<222> LOCATION: (480)
<220> FEATURE:
<221> NAME/KEY: unsure
<222> LOCATION: (483)
<220> FEATURE:
<221> NAME/KEY: unsure
```

```
<222> LOCATION: (496)
<220> FEATURE:
<221> NAME/KEY: unsure
<222> LOCATION: (498)
<220> FEATURE:
<221> NAME/KEY: unsure
<222> LOCATION: (500)
<220> FEATURE:
<221> NAME/KEY: unsure
<222> LOCATION: (519)
<220> FEATURE:
<221> NAME/KEY: unsure
<222> LOCATION: (533)
<220> FEATURE:
<221> NAME/KEY: unsure
<222> LOCATION: (539)
<220> FEATURE:
<221> NAME/KEY: unsure
<222> LOCATION: (563)

<400> SEQUENCE: 19
ggcggcggct acgtggggtg gcgacgacaa gctcattctg cgcggccttc agttccatgg      60
cttccacggt gtcctgcagg aggagaagac gttgggacag aagttcgtgg ttgacatcga     120
cgcctggata gacctcgccg ctgccggcga agtccgactg cattgctgac accgtcagct     180
acaccgatat ctacagcatt gcaaaggatg ttgtcgaggg cacgccacgc aacctcttgg     240
agtcggtagc tcactcnatc gcagaggcca cgctgctcaa gttccctcaa atctccgcag     300
tccgagtgaa ggttggcaag cctcacctcg cggtgcgagg cgttctggac taactgggcg     360
tggggataac naggcacaaa aagaaagaat tgagattctg tncacatgtg gtgatggggg     420
aaccagttca atnctgatgg nactgcnggc aanaccataa tccacccncc ccntgttgcn     480
tgntgggaac taagcnantn cctttcacct ctgaactgnt gggaatatcg ggnaatctng     540
ttcccctaaa ttgctttatt acna                                           564

<210> SEQ ID NO 20
<211> LENGTH: 116
<212> TYPE: PRT
<213> ORGANISM: Zea mays

<400> SEQUENCE: 20

Asp Lys Leu Ile Leu Arg Gly Leu Gln Phe His Gly Phe His Gly Val
 1               5                  10                  15

Leu Gln Glu Glu Lys Thr Leu Gly Gln Lys Phe Val Val Asp Ile Asp
                20                  25                  30

Ala Trp Thr Ser Pro Leu Pro Ala Lys Ser Asp Cys Ile Ala Asp Thr
            35                  40                  45

Val Ser Tyr Thr Asp Ile Tyr Ser Ile Ala Lys Asp Val Val Glu Gly
        50                  55                  60

Thr Pro Arg Asn Leu Leu Glu Ser Val Ala His Ser Ile Ala Glu Ala
65                  70                  75                  80

Thr Leu Leu Lys Phe Pro Gln Ile Ser Ala Val Arg Val Lys Val Gly
                85                  90                  95

Lys Pro His Leu Ala Val Arg Gly Val Leu Asp Leu Gly Val Gly Ile
            100                 105                 110

Thr Arg His Lys
        115

<210> SEQ ID NO 21
<211> LENGTH: 601
<212> TYPE: DNA
<213> ORGANISM: Glycine max
```

```
<220> FEATURE:
<221> NAME/KEY: unsure
<222> LOCATION: (406)
<220> FEATURE:
<221> NAME/KEY: unsure
<222> LOCATION: (413)
<220> FEATURE:
<221> NAME/KEY: unsure
<222> LOCATION: (450)
<220> FEATURE:
<221> NAME/KEY: unsure
<222> LOCATION: (479)
<220> FEATURE:
<221> NAME/KEY: unsure
<222> LOCATION: (491)
<220> FEATURE:
<221> NAME/KEY: unsure
<222> LOCATION: (493)
<220> FEATURE:
<221> NAME/KEY: unsure
<222> LOCATION: (514)
<220> FEATURE:
<221> NAME/KEY: unsure
<222> LOCATION: (520)
<220> FEATURE:
<221> NAME/KEY: unsure
<222> LOCATION: (539)
<220> FEATURE:
<221> NAME/KEY: unsure
<222> LOCATION: (579)
<220> FEATURE:
<221> NAME/KEY: unsure
<222> LOCATION: (585)

<400> SEQUENCE: 21
cggagaggcg agggagtgag ggactagcac agaaagatat tgtttggtgt acggtggtga      60
gtgtcgacgc tgccactctc gcctgtgtct gtgataaatg gaatctgatg caccgacatg     120
gggagacaaa ctcatgttga ggggattgtc attccatggt tttcatggag caaagcctga    180
agaaaggaca ctgggccaga agttcttcat agatatagat gcttggatgg atctcaaagc    240
agctgggcaa atctgatcac ttatcaaatt ctgttagtta cacagaaata tatgatatag    300
ctaaggatgt tcttgaaggg tcacctcaca atcctctggg agtcaagtgg gccaaaaaaa    360
ttgcaatcac tactcttaca aatcaaaaag aaatatctgc tgtccnagtg aanggtggga    420
aaccccatgt ggcaattccg ggtccaattn attacttaag cgtttgagaa tcctaaacnc    480
aaaaaccaac ntnttcaagg ctaaaaaatt taanatttan tgctgcacaa attttatant    540
ttcaaaatcc accttgatac aaaaagtaaa ggtactccnt tcccntcaag gccccaatta    600
g                                                                    601

<210> SEQ ID NO 22
<211> LENGTH: 67
<212> TYPE: PRT
<213> ORGANISM: Glycine max
<220> FEATURE:
<221> NAME/KEY: UNSURE
<222> LOCATION: (43)..(44)

<400> SEQUENCE: 22

Asp Lys Leu Met Leu Arg Gly Leu Ser Phe His Gly Phe His Gly Ala
 1               5                  10                  15
Lys Pro Glu Glu Arg Thr Leu Gly Gln Lys Phe Phe Ile Asp Ile Asp
             20                  25                  30
Ala Trp Met Asp Leu Lys Ala Ala Gly Gln Xaa Xaa His Leu Ser Asn
         35                  40                  45
Ser Val Ser Tyr Thr Glu Ile Tyr Asp Ile Ala Lys Asp Val Leu Glu
```

Gly Ser Pro
65

<210> SEQ ID NO 23
<211> LENGTH: 439
<212> TYPE: DNA
<213> ORGANISM: Triticum aestivum

<400> SEQUENCE: 23

| | | | | | | |
|---|---|---|---|---|---|---|
| ccaggttcca | ctccacccac | ccacctgcgc | cgccagctct | aaaggaggcg | gcgtcggccg | 60 |
| gcgggcgagc | gcacgcccag | gcccaatcga | tcgatcccag | ctctagaggg | gagggagcaa | 120 |
| ccatggcggg | ggacggggag | gacgaggtgc | cggcgatggg | cggagacaag | ctgatcctgc | 180 |
| ggggctgca | gttccacggc | ttccacggcg | tgaagcagga | ggagaagaag | ctgggccaga | 240 |
| agttcgtggt | cgacgtggac | gcctggatgg | acctcgccgc | cgccgggac | tccgacgaca | 300 |
| tcgcccacac | cgtcagctac | accgacatct | acaggatagc | caagggcgtg | gtggaaggcc | 360 |
| cgtcgcggaa | acctcctgga | gtcggtggcg | cagtcgatcg | ccggcaacaa | cgctgctccg | 420 |
| aagtttcccc | aaatctccg | | | | | 439 |

<210> SEQ ID NO 24
<211> LENGTH: 65
<212> TYPE: PRT
<213> ORGANISM: Triticum aestivum

<400> SEQUENCE: 24

Asp Lys Leu Ile Leu Arg Gly Leu Gln Phe His Gly Phe His Gly Val
 1               5                  10                  15

Lys Gln Glu Glu Lys Lys Leu Gly Gln Lys Phe Val Val Asp Val Asp
            20                  25                  30

Ala Trp Met Asp Leu Ala Ala Ala Gly Asp Ser Asp Asp Ile Ala His
        35                  40                  45

Thr Val Ser Tyr Thr Asp Ile Tyr Arg Ile Ala Lys Gly Val Val Glu
    50                  55                  60

Gly
 65

<210> SEQ ID NO 25
<211> LENGTH: 677
<212> TYPE: DNA
<213> ORGANISM: Zea mays
<220> FEATURE:
<221> NAME/KEY: unsure
<222> LOCATION: (565)
<220> FEATURE:
<221> NAME/KEY: unsure
<222> LOCATION: (643)
<220> FEATURE:
<221> NAME/KEY: unsure
<222> LOCATION: (656)
<220> FEATURE:
<221> NAME/KEY: unsure
<222> LOCATION: (676)

<400> SEQUENCE: 25

| | | | | | | |
|---|---|---|---|---|---|---|
| cctcgaacga | gggccgtacc | tagcgcctct | gtccttcgtc | ggccgtcgca | ctgtgctccc | 60 |
| gtccgcctcc | ggcctccgcc | aacccgcgtc | cgcccacgac | taggcggctc | tgggcaggtc | 120 |
| cttccacaaa | gatgtgaagg | attaaagctc | atgtgaaaga | ttctaagact | acaattggta | 180 |
| tcaagcggtt | gctttcttat | ttctcatacg | ctcaaccatg | ctcctgcatg | ctaaggattc | 240 |

-continued

```
agttaggaag atgcattcag ttgctaagaa ctactttgtg tctgatctta ctcatcctcc    300
aagatccttg aacagagctt ccagacatgt tgttccattc aagacccgtt tctttacgca    360
ttgctcactt gagagccgtt cagttgacca agagattgtg attgctatgg gaagcaatgt    420
aggcgataga gtcagtacat tcaacagggc attgcagctg atgaaaagct cagacgtgaa    480
catcactagg catgcctgtc tctatgaaac cgccctgct tatttgactg atcagccacg     540
gtttcttaac tctgccattc ggggnacaac taggctccag gccacatgag cttcttaaac    600
tggctaaagg aaattgagaa gggaattggc cgcactgggg ganataaagg tacggnccaa    660
gacctatcga ttaagna                                                   677
```

<210> SEQ ID NO 26
<211> LENGTH: 101
<212> TYPE: PRT
<213> ORGANISM: Zea mays
<220> FEATURE:
<221> NAME/KEY: UNSURE
<222> LOCATION: (69)
<220> FEATURE:
<221> NAME/KEY: UNSURE
<222> LOCATION: (92)..(93)

<400> SEQUENCE: 26

```
Ser Leu Glu Ser Arg Ser Val Asp Gln Glu Ile Val Ile Ala Met Gly
 1               5                  10                  15

Ser Asn Val Gly Asp Arg Val Ser Thr Phe Asn Arg Ala Leu Gln Leu
            20                  25                  30

Met Lys Ser Ser Asp Val Asn Ile Thr Arg His Ala Cys Leu Tyr Glu
        35                  40                  45

Thr Ala Pro Ala Tyr Leu Thr Asp Gln Pro Arg Phe Leu Asn Ser Ala
    50                  55                  60

Ile Arg Gly Thr Xaa Ala Pro Gly His Met Ser Phe Leu Asn Trp Leu
65                  70                  75                  80

Lys Glu Ile Glu Lys Gly Ile Gly Arg Thr Gly Xaa Xaa Arg Tyr Gly
                85                  90                  95

Pro Arg Pro Ile Asp
            100
```

<210> SEQ ID NO 27
<211> LENGTH: 227
<212> TYPE: DNA
<213> ORGANISM: Oryza sativa
<220> FEATURE:
<221> NAME/KEY: unsure
<222> LOCATION: (125)
<220> FEATURE:
<221> NAME/KEY: unsure
<222> LOCATION: (176)
<220> FEATURE:
<221> NAME/KEY: unsure
<222> LOCATION: (181)
<220> FEATURE:
<221> NAME/KEY: unsure
<222> LOCATION: (188)
<220> FEATURE:
<221> NAME/KEY: unsure
<222> LOCATION: (190)
<220> FEATURE:
<221> NAME/KEY: unsure
<222> LOCATION: (220)
<220> FEATURE:
<221> NAME/KEY: unsure
<222> LOCATION: (222)

```
<400> SEQUENCE: 27
cttacagttt aggtgcttca catgtgccaa ttttacttgg accctcaagg aaaagatttt      60
taggtgaaat atgcaatcgt gtcaatccca ctgagagaga tgctgctacc atggtcgttg     120
ctacngctgg gatattgaat ggtgctaata tagtaagggt gcataatgtt aaatanggct     180
nggatacngn aaaggtctct aatcctttgc caaaggggan angtgtt                   227

<210> SEQ ID NO 28
<211> LENGTH: 70
<212> TYPE: PRT
<213> ORGANISM: Oryza sativa
<220> FEATURE:
<221> NAME/KEY: UNSURE
<222> LOCATION: (57)
<220> FEATURE:
<221> NAME/KEY: UNSURE
<222> LOCATION: (59)
<220> FEATURE:
<221> NAME/KEY: UNSURE
<222> LOCATION: (62)

<400> SEQUENCE: 28

Ser Leu Gly Ala Ser His Val Pro Ile Leu Leu Gly Pro Ser Arg Lys
 1               5                  10                  15

Arg Phe Leu Gly Glu Ile Cys Asn Arg Val Asn Pro Thr Glu Arg Asp
            20                  25                  30

Ala Ala Thr Met Val Val Ala Thr Ala Gly Ile Leu Asn Gly Ala Asn
        35                  40                  45

Ile Val Arg Val His Asn Val Lys Xaa Gly Xaa Asp Thr Xaa Lys Val
    50                  55                  60

Ser Asn Pro Leu Pro Lys
 65                  70

<210> SEQ ID NO 29
<211> LENGTH: 534
<212> TYPE: DNA
<213> ORGANISM: Zea mays
<220> FEATURE:
<221> NAME/KEY: unsure
<222> LOCATION: (8)
<220> FEATURE:
<221> NAME/KEY: unsure
<222> LOCATION: (14)..(15)
<220> FEATURE:
<221> NAME/KEY: unsure
<222> LOCATION: (26)
<220> FEATURE:
<221> NAME/KEY: unsure
<222> LOCATION: (49)
<220> FEATURE:
<221> NAME/KEY: unsure
<222> LOCATION: (182)
<220> FEATURE:
<221> NAME/KEY: unsure
<222> LOCATION: (189)
<220> FEATURE:
<221> NAME/KEY: unsure
<222> LOCATION: (271)
<220> FEATURE:
<221> NAME/KEY: unsure
<222> LOCATION: (285)
<220> FEATURE:
<221> NAME/KEY: unsure
<222> LOCATION: (321)..(322)
<220> FEATURE:
<221> NAME/KEY: unsure
<222> LOCATION: (342)
<220> FEATURE:
<221> NAME/KEY: unsure
```

```
<222> LOCATION: (413)
<220> FEATURE:
<221> NAME/KEY: unsure
<222> LOCATION: (500)
<220> FEATURE:
<221> NAME/KEY: unsure
<222> LOCATION: (510)
<220> FEATURE:
<221> NAME/KEY: unsure
<222> LOCATION: (512)
<220> FEATURE:
<221> NAME/KEY: unsure
<222> LOCATION: (517)
<220> FEATURE:
<221> NAME/KEY: unsure
<222> LOCATION: (529)

<400> SEQUENCE: 29
catggctncc aaannttcgg cactanacgt actgagaaga gctcgcgtnc ccgctactcg      60
ccggcccacc tccgggcgcc tgctcctcct ctctccctcc gcccacctca tcatcatccg    120
ccgcgccatg gcctccgccg ccgccgcgca ggcgcagcag gtggcgcccc accggcgacc    180
gnggagtang aggaggtgct ggggcggctc tcctcgctca tcacgcagaa ggtgcgcgcg    240
aacagcgcca accgcggcaa ccagtgggac ntcatggagc actangtcaa gattctggag    300
ctggaggagt cgatcgcgcg nnatgaaagt gattcacgtc gnagggacca aggggaaggg    360
ttccacatgc acattcaccg agtcaatcct gcgatcgtgt ggcttccata atnggctgtt    420
taactcacca acatttgatt ggatgttaga gagcgaattc agctagattg gggttaataa    480
tttctgaaga gaaattttn aagtactctn gntgtgntgg aacaagttna agga          534

<210> SEQ ID NO 30
<211> LENGTH: 36
<212> TYPE: PRT
<213> ORGANISM: Zea mays
<220> FEATURE:
<221> NAME/KEY: UNSURE
<222> LOCATION: (7)
<220> FEATURE:
<221> NAME/KEY: UNSURE
<222> LOCATION: (31)

<400> SEQUENCE: 30

Met Lys Val Ile His Val Xaa Gly Thr Lys Gly Lys Gly Ser Thr Cys
 1               5                  10                  15
Thr Phe Thr Glu Ser Ile Leu Arg Ser Cys Gly Phe His Asn Xaa Leu
            20                  25                  30
Phe Asn Ser Pro
        35

<210> SEQ ID NO 31
<211> LENGTH: 553
<212> TYPE: DNA
<213> ORGANISM: Glycine max
<220> FEATURE:
<221> NAME/KEY: unsure
<222> LOCATION: (520)
<220> FEATURE:
<221> NAME/KEY: unsure
<222> LOCATION: (549)

<400> SEQUENCE: 31
ggcttctcag ttaaatgtac ctcttcaagt ggtaacccca ttagatgcca aattgctaaa     60
tggttcaaga ctagcgcttg gaggtgaaca ccaatatata aatgctggtc ttgctattgc    120
attatgctct acgtggctga aaatgaatgg gcatcttgaa gactcgtact tgaaacatat    180
```

```
acaacacact ttaccagaga agttcataaa agggttaaca actgcaagtt tgcaaggaag      240
ggctcagatt gttcctgatc agttcatcaa tgatgaaata ccaaatgaac ttgtcttctt      300
tttagatggg gctcatagtc ctgaaagcat ggaagcatgt gccaggtggt tttctcttgc      360
tattaaagat caagaccaga ttttgtttca tcaagaaact tgataattct aacttctcaa      420
accaagtagt gaagatgcac aatggtgaaa ctgtacagaa gaaatccaca cagattttgc      480
tgttcaattg tatgtctgag cgaaaccctc aattgcttcn tccccacttg atgaaaacat      540
gtgctgatna agg                                                        553

<210> SEQ ID NO 32
<211> LENGTH: 24
<212> TYPE: PRT
<213> ORGANISM: Glycine max

<400> SEQUENCE: 32

Leu Ala Leu Gly Gly Glu His Gln Tyr Ile Asn Ala Gly Leu Ala Ile
  1               5                  10                  15

Ala Leu Cys Ser Thr Trp Leu Lys
                20
```